United States Patent [19]

Hickmann

[11] Patent Number: 4,577,628

[45] Date of Patent: Mar. 25, 1986

[54] OXYGEN DOME FOR SMALL ANIMALS

[76] Inventor: Horst R. Hickmann, 1455 Montegor, Cincinnati, Ohio 45230

[21] Appl. No.: 704,740

[22] Filed: Feb. 25, 1985

[51] Int. Cl.4 .............................................. A61M 16/00
[52] U.S. Cl. ............................ 128/205.26; 128/200.14
[58] Field of Search ....................... 128/205.26, 202.12, 128/200.14, 1 B, 205.25, 204.18

[56] References Cited

U.S. PATENT DOCUMENTS

| | | | |
|---|---|---|---|
| D. 243,364 | 2/1977 | Miller | 128/205.26 |
| 3,680,557 | 8/1972 | Donigvian | 128/205.26 |
| 4,343,304 | 8/1982 | Hickmann | 128/200.14 |
| 4,407,280 | 10/1983 | Trammell et al. | 128/205.26 |

FOREIGN PATENT DOCUMENTS

| | | | |
|---|---|---|---|
| 873874 | 7/1942 | France | 128/205.26 |
| 849636 | 9/1960 | United Kingdom | 128/205.26 |

*Primary Examiner*—Henry J. Recla
*Attorney, Agent, or Firm*—Frost & Jacobs

[57] ABSTRACT

A veterinarian inhalation device for small animals comprising a dome having a first spherically shaped closed end portion and an opposite semicylindrically shaped open end portion and having one or more orifices for the introduction of air, oxygen, nebulized medicine or the like. The dome includes semicircular arcuate ribs which project inwardly into the interior of the dome so as to act as a curtain to aid in maintaining the concentration of any gases which may be introduced into the interior of the dome. The dome may be made of clear, light weight plastic, thus permitting the veterinarian to view the small animal as desired.

14 Claims, 5 Drawing Figures

OXYGEN DOME FOR SMALL ANIMALS

BACKGROUND OF THE INVENTION (1) Field of the Invention

The present invention relates to veterinary inhalation therapy apparatus and in particular to a device to treat small animals with a high concentration of oxygen or air with or without nebulized fluid. Additionally, the device includes an inlet for an anesthetic.

(2) Prior Art

Generally, post surgical treatment for small animals includes inhalation therapy. Previously, it was necessary to place the small animal in an intensive care kennel or other similar confining system in which the veterinarian has limited access to the small animal in order to provide inhalation therapy.

U.S. Pat. No. 2,847,993 to Woodruff is exemplary of a prior art intensive care cage for small animals capable of providing inhalation therapy. The cage is shaped substantially like a box and is provided with a clear transparent plexiglass window in the top wall. A hinged door in a vertical wall at one end of the box provides egress and ingress to the interior thereof. A small opening at the opposite end of the cage is for the introduction of nebulized medicant, or the like. However, this device does not permit the veterinarian to have easy access to the small animal therein without removing the animal from the cage.

Other devices used by humans for inhalation therapy consist of clear plastic shields which are designed to partially cover the nose and mouth. The shields include at least one orifice for introducing a nebulized or atomized medicant. These devices are typically self-employed by those who have asthma, for example, and are in need of medicinal relief. The following patent reference is exemplary thereof.

U.S. Pat. No. 3,182,659 to Blount discloses an oxygen inhalation mask or shield shaped to extend beneath the jaw or chin of an adult and extend entirely around and over the mouth and nose. The mask or shield includes an orifice positioned in the vicinity of the mouth and nose which is coupled to a cylindrical oxygen inlet tube to supply the patient with oxygen and/or other medicinal nebulized drugs. The cylindrical oxygen inlet tube is connected to a source of oxygen and/or a source of drugs. However, this device is too small and too irregular in shape to be employed for small animals.

A need exists for a housing for small animals in need of inhalation therapy which permits the veterinarian to have ready access to the small animal. Having access to the small animal is particularly beneficial after operative surgery, for example, so that the veterinarian may readjust a medical implement, or change a bandage.

SUMMARY OF THE INVENTION

The present invention consists of a clear transparent plastic dome which is provided with a plurality of orifices positioned at desired locations on the dome surface to provide air, humidified oxygen, and atomized or nebulized medicant. Optionally, other orifices may be desirable to exhaust excess or exhaled gases. The dome is generally a hollow shell having a first spherically shaped closed end portion and an opposite semi-cylindrically shaped open end portion. The dome includes a circumferential, inwardly projecting rib adjacent the open end thereof. If desirable, the dome may be secured to a heavy weight made of aluminum, for example, so as to anchor the dome while in use. Additionally, an inlet block is associated with one of the orifices and is provided with an impact tab upon which introduced anesthetic or other medicant impinges and diffuses into the interior of the dome.

In the broadest sense, the present invention comprises a dome designed to fit over a small animal or over at least the nose of a small animal. The dome includes a plurality of orifices for introducing one or more gases, such as air, oxygen, atomized or nebulized medicant, and for permitting excess and exhaled gases to exhaust from the interior of the dome. Additionally, the dome includes an inwardly projecting circumferential rib which acts as a curtain to retain the atomized or nebulized medicant, or the air or oxygen within the dome.

PREFERRED EMBODIMENTS OF THE INVENTION

Figure 1:
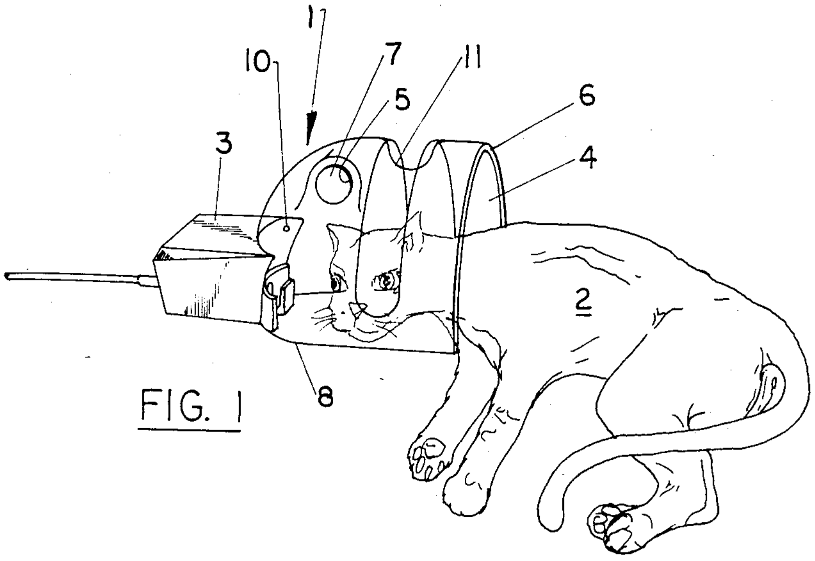
FIG. 1 is a perspective view of the dome positioned over the head of a small animal.

As illustrated in FIG. 1, a dome having a first spherically shaped closed end portion and an opposite semi-cylindrically shaped open end portion is generally represented by reference numeral 1. The dome is a hollow shell structure, sized to permit a small animal to occupy at least a portion of the interior space under the dome. For example, the dome could be placed upon a horizontal surface with its truncated edge adjacent a vertical surface, such as a wall, thereby blocking the access opening so that the dome serves as an intensive care structure for a small bird. Other pets, for example, guinea pigs or hampsters would also be capable of fitting within the interior of the dome. Lastly, the dome is capable of fitting over the head of small cats and dogs to function as an oxygen tent during inhalation therapy. For animals such as larger dogs, the dome is sized to fit over the nose and about the mouth so that these animals may also benefit from inhalation therapy necessary, for example, after a post-surgical procedure.

The truncated semispherical dome can be made from many different types of materials, namely, metals, plastics, synthetic resins or composites. If the dome is made from iron, for example, it would be necessary to coat the dome so that it would not rust when humidified oxygen or humidified air is introduced therein. Moreover, it would be necessary to coat the dome in order to avoid the reaction of any introduced medicants or drugs with the dome itself. Preferably, the dome is made of plastic because it may be easily molded or otherwise shaped, and it can be transparent so that the veterinarian can view the small animal through the dome. Plastic is essentially inert to most medicants and drugs so that no coating is necessary. Furthermore, a plastic dome can easily be cleaned and sterilized for repetitive use, and it is sufficiently strong to withstand any abuse from a small animal. Because the plastic can be transparent, it does not readily frighten an animal in therapy because the interior would not be dark as is the case with metal domes, for example. Of the plastics suitable for use in manufacturing the dome, the preferred plastic is UVEX TM, which is a high impact cellulose acetate butyrate transparent plastic capable of being vacuum molded.

When plastic is employed in the manufacturing of the dome, it is often necessary to anchor the plastic so that a small animal will not accidentally move or overturn the dome. Moreover, the plastic dome must be firmly anchored when employed as an intensive care housing for small animals, such as hamsters, in order to prevent their escape. Accordingly, a weight is firmly secured to the rear of the dome. The weight may consist of any appropriate material, with aluminum being preferred because it does not oxidize or rust like iron, and is more chemically stable than lead, for example. Brass and copper are also acceptable metal weights, but these are more costly than aluminum.

The shape of the weight may take any form. Preferentially, however, the surface of the weight which contacts the rear surface of the dome should mate with the rear portion of the dome, in order to firmly secure the dome to the weight.

As illustrated in FIG. 1, the dome 1 is positioned over the head of a small animal 2, so that anesthetic, for example, can be introduced into the breathing passages of the small animal. The dome is anchored firmly in position by means of the weight 3 which is attached to the rear of the dome in a manner to be described more fully hereinafter.

Figure 2:
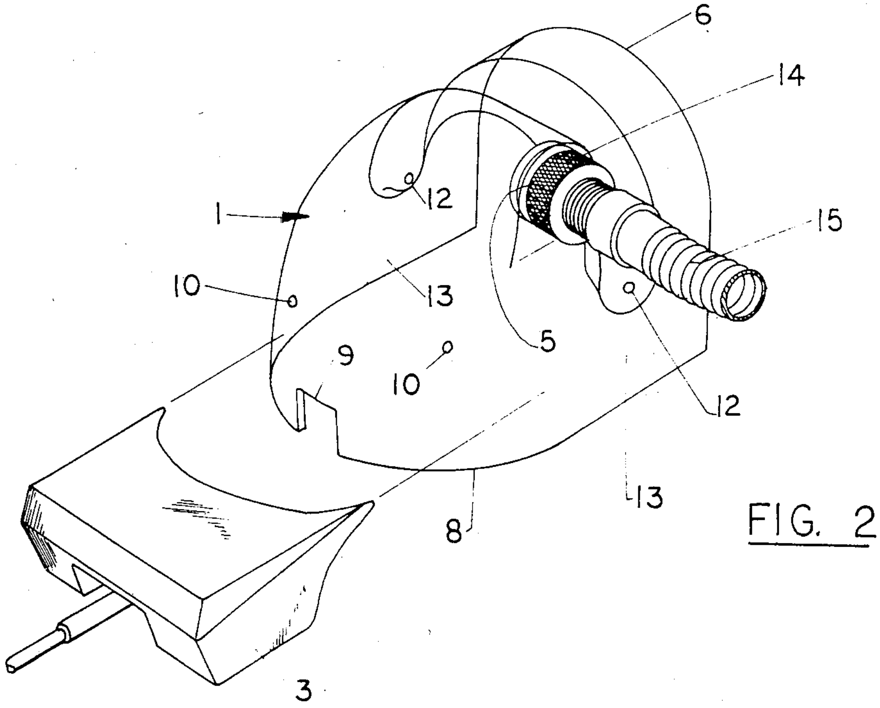
FIG. 2 is a rear exploded perspective view of the dome and weight, including an adapter coupled to the dome and to a large flexible supply conduit.
Figure 3:
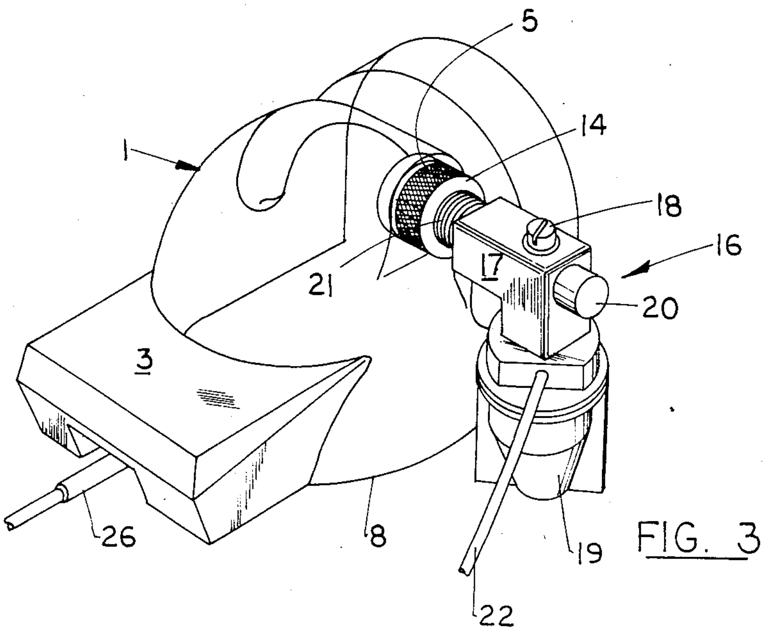
FIG. 3 is a rear perspective view of the dome of the present invention, including an adapter coupled to the dome and a nebulizer manifold.

The transparent plastic dome 1, as illustrated in FIGS. 1, 2 and 3, is a truncated semispherical dome having a semicircular opening 4 formed within the dome when the dome rests upon a flat surface. As shown in FIG. 1, the head of the small animal 2 is positioned within the interior of the dome through opening 4.

The dome is provided with a plurality of holes for various purposes as described herein. A hole 5 extends through the truncated semispherical dome near the top thereof, spaced a suitable distance away from the semicircular truncated edge 6, which forms the opening 4. Hole 5 provides an inlet for the introduction of air or oxygen which may be humidified.

As illustrated in FIG. 1, the dome 1 is employed as an anesthesia tent following post operative surgery in order to slowly bring a small animal back to consciousness. When the dome is employed in this manner, a plug 7 is inserted into hole 5 in order to preclude the anesthesia from escaping therethrough and thus, from escaping past the breathing passages of the small animal. The U-shaped bottom edge 8 of the dome is in contact with a flat surface and is provided with a rectangular opening 9 (see FIG. 2) at the bight of the U-shaped edge 8. It will, of course, be understood that this opening may be any shape suitable to permit the introduction of anesthesia into the interior of the dome 1.

Positioned above and to either side of the opening 9 are a pair of holes 10 in the dome 1 (only one of which is illustrated in FIG. 1) for fastening the weight 3 to a rear portion of the dome 1. Corresponding holes 10*a* (best illustrated in FIG. 4) are formed in the weight 3 and positioned in alignment with holes 10 so that a bolt, or the like, may securely fasten the dome to the weight 3.

A circumferential arcuate rib 11 is provided adjacent semicircular edge 6 between hole 5 and edge 6. The rib 11 extends from one side of the dome 1 near U-shaped edge 8, to the other side of the dome 1 near U-shaped edge 8, thus forming an arcuate rib. The rib 11 projects inwardly, i.e., toward the inside of the dome 1, and serves not only to mechanically strengthen the overall structure of the dome 1, particularly in the area around semicircular edge 6, but also acts as a curtain to help retain the gases such as air or oxygen and the anesthetic. In this fashion, the curtain aids in maintaining the concentration of air or oxygen, and the anesthetic, within the dome 1 as may be required or desired. Optionally, the dome may include a pair of holes 12 (see FIG. 2) in the arcuate rib 11 near each end thereof, to aid in the escape of carbon dioxide expelled from any small animal and any excess gases. In particular, holes 12 are necessary when the dome 1 is employed as an intensive care unit for small animals such as birds, hamsters or guinea pigs wherein the U-shaped edge 8 rests upon a flat surface, while the semicircular edge 6 abuts a vertical wall, thus enclosing the interior space of the dome 1.

When the dome 1 is employed as an oxygen tent for small animals such as cats and small dogs, the expelled air and excess gases escape from the interior of the dome through the space between the bottom portion of arcuate rib 11 and the animal's head (as illustrated in FIG. 1), and between the portion 13 of dome 1, located below the arcuate rib 11, and the head of the animal. Portion 13 is the primary exit for expelled air and excess gases when the head of the animal is large so as to be in close proximity to the arcuate rib 11, thereby preventing the escape of gases.

As shown in FIG. 2, an adapter 14 is coupled to the dome 1 through hole 5. The adapter is substantially the same as the adapter set forth in U.S. Pat. No. 4,343,304 to Hickmann. As illustrated in FIG. 2, the adapter 14 is coupled with a large flexible supply conduit 15, which in turn is coupled with a source of air or oxygen (not shown) Note that plug 7 has been removed from the FIG. 2 operation so as to permit the adapter 14 to couple to the dome.

In the FIG. 3 modification, the dome is employed to provide the small animal with humidified air or oxygen, or a nebulized medicant carried by air or oxygen, and an anesthetic gas. If the small animal is anesthetized for a period of time sufficiently long enough to cause the animal's respiratory passages to dry out due to lack of moisture in the source of air, oxygen or anesthetic, the nebulizer, as shown in FIG. 3, is employed. As shown in FIG. 3, the adapter 14 is coupled with a nebulizing device generally illustrated by reference numeral 16. The nebulizer device 16 is substantially the same as that disclosed in U.S. Pat. No. 4,434,304 to Hickmann. When employed, the nebulizer device 16 introduces humidified air or oxygen, or a nebulized medicant with air or oxygen into the interior of the dome 1. When employed as a humidifier, the respiratory passages of the animal will not become dry because the precise amount of water vapor may be accurately controlled by the nebulizer device 16. When employed as a dosing device, the nebulizer device 16 is capable of accurately maintaining a preselected concentration of medicant mixed with air or oxygen, within the interior of the dome 1.

The nebulizer device 16 comprises a base 17 having a filler cap 18 for filling the reservoir 19 with a humidifying liquid, namely water or a water base solution, or a medicant such as a pain killer. The base also includes an inlet 20 for air or oxygen and an outlet 21 for the humidified air or oxygen. Optionally, an additional gas inlet tube 22 may be employed to provide a mixture of gase such as air and oxygen or air and anesthetic gas, or the like, as may be desired.

Figure 4:
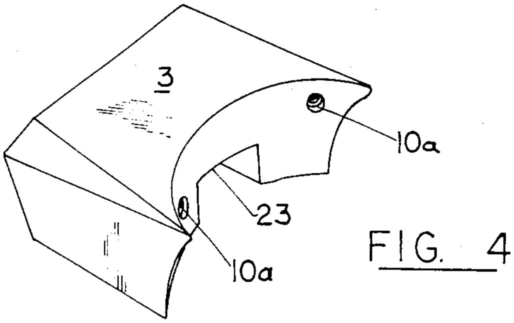
FIG. 4 is a frontal perspective view of the dome weight employed to anchor the dome firmly in position.

FIG. 4 illustrates the weight 3. The weight 3 is provided with a pair of orifices 10*a* which are designed to mate with holes 10 of the dome 1. In this manner, the dome 1 and weight 3 may be securely fastened to one another by screws (not shown). The weight 3 also includes a passageway 23 whose cross-sectional area is substantially the same as opening 9 in dome 1. Passageway 23 is designed to just nicely surround a portion of the anesthetic inlet member 24, shown in FIG. 5.

Figure 5:
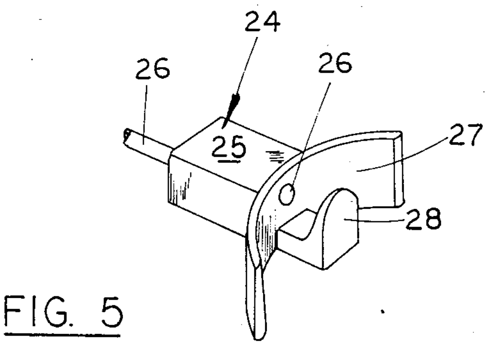
FIG. 5 is an upper elevational perspective view of the inlet block including the impact tab.

As illustrated in FIG. 5, the anesthetic inlet member, generally indicated by reference numeral 24, includes a foundation extension arm 25 which projects from the interior of the dome, through opening 9 and into the passageway 23 of the weight 3. The arm 25 includes an integrally formed conduit 26 which is coupled to a source of anesthesia (not shown). The anesthesia inlet member 24 also comprises an arcuate wall 27 which is shaped substantially like that of the bight portion of the dome 1 adjacent edge 8 and is attached to one end of arm 25. Conduit 26 also projects through the arcuate wall 27 and terminates in an opening in the center of the interior of the arcuate wall. The anesthetic inlet member 24 also includes an integrally projecting tab 28 which is integrally formed with the arcuate wall 27 in the bight area thereof. The tab 28 has a lower portion attached to wall 27, while an upper portion is positioned in such a manner that it projects in front of or is in alignment with the outlet in the arcuate wall of the conduit 26. The surface of the tab 28 facing the conduit 26 is rounded so that anesthesia exiting the outlet impacts upon the tab 28 and is dispersed outwardly in all directions.

In operation of the dome 1 illustrated in FIG. 1, the weight 3 is first securely attached to the dome 1 by aligning the apertures 10*a* of the weight 3 with the holes 10 of the dome 1, and properly securing the dome 1 to the weight 3 in any conventional manner such as with screws or the like. The anesthetic inlet member 24 is then coupled to a source of anesthetic (not shown). The anesthetic inlet member 24 is positioned with respect to dome 1 and weight 3, so that the arcuate wall 27 is on the inside of the dome, while the arm member 25 projects through opening 9 of dome 1. The weight 3 is positioned over the projecting portion of the arm 25 so that it projects into the passageway 23. If the dome is only employed during or after post operative surgery for a short period of time for maintaining the animal in an anesthetized condition, the orifice 5 is capped with plug 7. The dome is now ready to be employed as an anesthetic tent by placing the dome over the head of a small animal, or placing the animal within the interior of the dome, when the dome is adjacent a vertical surface.

When it is desirable to provide the small animal with air or oxygen, the plug 7 is removed from the hole 5 and the adaptor 14 is coupled to the dome through hole 5 and coupled to a source of air or oxygen (not shown) by the use of the flexible conduit 15. In this manner, as illustrated in FIG. 2, the device is ready to use for bringing a small animal out of unconsciousness after post operative surgery by mixing the anesthetizing gas with oxygen or air in the proper proportions to slowly bring the small animal to consciousness.

When it is desired to employ humidified air or oxygen or a medicant with air or oxygen in addition to an anesthetizing gas, as illustrated in FIG. 3, the plug 7 is removed from hole 5 and adapter 14 is coupled with hole 5 and the nebulizer device 16. The filler cap 18 is removed and liquid medicant or water, or both, is added to the nebulizer reservoir 19. The cap 18 is replaced and the flexible supply conduit 15 is attached to inlet 20. The nebulizer device 16 is now ready for operation. If desired, an additional gas can be introduced into the interior of the dome through inlet tube 22.

With reference to FIGS. 1, 2 and 3, the dome 1 is capable of supplying a small animal with either an anesthetizing gas; air or oxygen; humidified air, oxygen or anesthetic gas; or the combinatin of any of these.

Modifications of the present invention described herein may be made without departing from the scope of it.

What is claimed is:

1. A dome to be used in inhalation therapy for small animals comprising:

a dome having a first closed end portion and an opposite open end portion, said closed end portion being spherically shaped, said open end portion being semi-cylindrically shaped, said dome having at least one orifice for introducing one or more gases into the interior of the dome and a semicircular arcuate rib projecting into the interior of the dome, said at least one orifice being located between said rib and said closed end whereby said rib serves as a curtain to aid in maintaining any gas introduced into the interior of the dome through said at least one orifice, said open end portion terminating in a semicircular opening of sufficient size to permit the introduction of a small animal into the interior of said dome, said semicircular rib being spaced in close proximity to said semicircular opening.

2. The dome of claim 1, wherein said at least one orifice includes a large circular aperture near the top portion of said dome for the introduction of air or oxygen.

3. The dome of claim 2, wherein said at least one orifice includes a bore in the bight area of said closed end portion for the introduction into the interior of the dome of an anesthetic.

4. The dome of claim 3, wherein said at least one orifice includes a plurality of small holes in the semicircular arcuate rib for aiding in the escape of exhaust or excess gases.

5. An inhalation therapy device for administering any one of air, oxygen, humidified air, humidified oxygen, an anesthetic, a nebulized medicant with air or oxygen, or a combination of any one of these, to small animals comprising:

a dome having a first closed end portion and an opposite open end portion, said closed end portion being spherically shaped, said open end portion being semi-cylindrically shaped, said dome, having at least one orifice for introducing one or more of said gases into the interior of said dome, and a semicircular arcuate rib projecting into the interior of the dome, said at least one orifice being located between said rib and said closed end whereby said rib serves as a curtain to aid in maintaining any gas introduced into the interior of the dome through said at least one orifice, said open end portion terminating in a semicircular opening of sufficient size to permit the introduction of a small animal into the interior of the dome; said at least one orifice including a large circular aperture near the top portion of said dome for the introduction of air or oxygen;

an adaptor fitting into said opening and sealing said opening, said adaptor including means to couple a flexible conduit, a flexible conduit connected to a source of gas and to said coupling means, whereby a gas may be introduced into the interior of said dome through said flexible conduit and through said adaptor.

6. The device of claim 5, wherein said at least one orifice includes a bore in the bight area of the closed end portion, and an anesthetic inlet member fitted within said bore and adapted to be coupled with a supply of anesthetic, whereby the anesthetic may be introduced into the interior of the dome through the anesthetic inlet member and said bore.

7. The device of claim 6, wherein said anesthetic inlet member includes a longitudinal arm having a conduit extending longitudinally therethrough, an arcuate wall integrally secured to one end of said arm so that said conduit also extends through said arcuate wall, and a diffusion tab integrally connected to said arcuate wall and being in position to permit any gas or anesthetic introduced into said conduit to impinge upon said diffusion tab, so that anesthetic introduced into the interior of said dome impinges upon said diffusion tab in order to adequately disperse the anesthesia over the entire volume of the interior of the dome.

8. The device of claim 7, further including a weight attached to the outside of said dome in the bight area thereof, said weight including a passageway in the bottom portion thereof sized so as to just nicely fit over and surround said arm of said anesthetic inlet member.

9. The device of claim 8, wherein said arcuate wall of said anesthetic inlet member is in continuous contact with said interior portion of said dome adjacent said bight area of said dome, while said weight is complementarily shaped with respect to the outside portion of the bight area of the dome, so that said dome is sandwiched between said weight and said arcuate wall of said anesthetic inlet member.

10. An inhalation therapy device for introducing any one of air, oxygen, humidified air, humidified oxygen, an anesthetic, a nebulized medicant with air or oxygen, or combination of any one of these, to small animals comprising:

a dome having a first closed end portion and an opposite open end portion, said closed end portion being spherically shaped, said open end portion being semi-cylindrically shaped, said dome, having at least one orifice for introducing one or more of said gases into the interior of said dome, and a semicircular arcuate rib projecting into the interior of the dome, said at least one orifice being located between said rib and said closed end whereby said rib serves as a curtain to aid in maintaining any gas introduced into the interior of the dome through said at least one orifice, said open end portion terminating in a semicircular opening of sufficient size to permit the introduction of a small animal into the interior of the dome; said at least one orifice including a large circular aperture near the top portion of said dome for the introduction of air or oxygen;

an adaptor fitting into said circular aperture and sealing said opening, said adaptor including a nebulizer unit attached to said adaptor, said nebulizer unit including a reservoir for water or medicant, an inlet cap in said nebulizer unit to provide access to said reservoir, a gas inlet in said nebulizer unit for introducing gas into the interior of said nebulizer unit so that it may become humidified, or serve as a carrier for a medicant, a flexible tube coupled to said gas inlet for introducing into the nebulizer unit a carrier gas designed to pick up a medicant or water vapor from the reservoir and introduce the carrier gas into the interior of said dome through said aperture.

11. The device of claim 10, wherein said at least one orifice includes a bore in the bight area of the closed end portion, and an anesthetic inlet member fitted within said bore and adapted to be coupled with a supply of anesthetic, whereby the anesthetic may be introduced into the interior of the dome through the anesthetic inlet member and said bore.

12. The device of claim 11, wherein said anesthetic inlet member includes a longitudinal arm having a conduit extending longitudinally therethrough, an arcuate wall integrally secured to one end of said arm so that said conduit also extends through said arcuate wall, and a diffusion tab integrally connected to said arcuate wall and being in position to permit any gas or anesthetic introduced into said conduit to impinge upon said diffusion tab, so that anesthetic introduced into the interior of said dome impinges upon said diffusion tab in order to adequately disperse the anesthesia over the entire volume of the interior of the dome.

13. The device of claim 12, further including a weight attached to the outside of said dome in the bight area thereof, said weight including a passageway in the bottom portion thereof sized so as to just nicely fit over and surround said arm of said anesthetic inlet member.

14. The device of claim 13, wherein said arcuate wall of said anesthetic inlet member is in continuous contact with said interior portion of said dome adjacent said bight area of said dome, while said weight is complemenarily shaped with respect to the outside portion of the bight area of the dome, so that said dome is sandwiched between said weight and said arcuate wall of said anesthetic inlet member.

* * * * *